United States Patent [19]
Suzuki et al.

[11] Patent Number: 5,746,730
[45] Date of Patent: May 5, 1998

[54] ABSORBENT ARTICLE AND METHOD OF MANUFACTURING ARTICLE

[75] Inventors: Migaku Suzuki, Kanagawa; Hiroaki Fukui, Saitama, both of Japan

[73] Assignee: Paragon Trade Brands, Inc.

[21] Appl. No.: 553,636

[22] PCT Filed: Jun. 3, 1994

[86] PCT No.: PCT/US94/06230

§ 371 Date: Mar. 5, 1996

§ 102(e) Date: Mar. 5, 1996

[87] PCT Pub. No.: WO94/28845

PCT Pub. Date: Dec. 22, 1994

[30] Foreign Application Priority Data

Jun. 3, 1993 [JP] Japan .................. 5-156343

[51] Int. Cl.$^6$ .................. A61F 13/15
[52] U.S. Cl. .................. 604/385.2; 604/385.1; 604/393
[58] Field of Search .................. 604/385.1, 385.2, 604/386, 387, 388, 389, 390, 391, 393, 394, 396

[56] References Cited

U.S. PATENT DOCUMENTS

| | | |
|---|---|---|
| Re. 26,151 | 1/1967 | Duncan et al. . |
| D. 346,021 | 4/1994 | Liberman et al. . |
| 3,196,874 | 7/1965 | Hrubecky . |
| 3,710,797 | 1/1973 | Marsan . |
| 3,807,402 | 4/1974 | Miller et al. . |
| 3,848,599 | 11/1974 | Schaar .................. 604/385.1 |
| 3,926,189 | 12/1975 | Taylor . |
| 4,029,100 | 6/1977 | Karami .................. 604/389 |
| 4,427,408 | 1/1984 | Karami et al. . |
| 4,938,755 | 7/1990 | Foreman . |
| 4,938,757 | 7/1990 | Van Gompel et al. . |
| 4,950,263 | 8/1990 | Lewis .................. 604/385.1 |
| 5,080,741 | 1/1992 | Nomura et al. . |
| 5,207,663 | 5/1993 | McQueen . |
| 5,440,764 | 8/1995 | Matsushita . |
| 5,451,217 | 9/1995 | Fujioka et al. . |

FOREIGN PATENT DOCUMENTS

| 6063072 | 3/1994 | Japan .................. 604/385.1 |
|---|---|---|

*Primary Examiner*—Mark Polutta
*Attorney, Agent, or Firm*—Hunton & Williams

[57] ABSTRACT

An absorbent article comprising a main body having a waist hole and a pair of leg holes, an elastic waist portion disposed along the, waist hole and a leg gather disposed along each of the leg holes. The main body comprises a front section and a rear section joined to each other in a crotch region and side regions of the main body. The front section has at least one constituent element whose property is different from that of the corresponding element of the rear section. The absorbent article is fully responsive to a variety of article configurations or constructions which require the front and rear sections to function differently or individually. A method for manufacturing such an absorbent article is also disclosed.

12 Claims, 15 Drawing Sheets

ABSORBENT ARTICLE AND METHOD OF MANUFACTURING ARTICLE

BACKGROUND OF THE INVENTION

The present invention relates to an absorbent article such as an infant diaper or an adult diaper, and further to a method for manufacturing such an absorbent article.

Absorbent articles, particularly infant and adult diapers include separate-type diapers and integral-type or tapeless-type diapers. The separate-type diaper is constructed to be separable from opposite sides of its waist region so that it can be developed into a flat configuration, and includes fastening tapes for releasably connecting front and rear waist regions of the diaper when applying the diaper to a user's body. The tapeless-type diaper is a pant-type diaper which includes a waist hole and a pair of leg holes. Both the separate-type and the tapeless-type diapers include a main body which comprises a liquid impermeable backsheet, a liquid permeable and hydrophobic topsheet superposed onto the backsheet and an absorbent core interposed between the topsheet and the backsheet. The main body is configured to include an elasticized waist portion and a pair of leg holes. Especially, the tapeless-type diapers have recently gained increased acceptance from consumers for their advantageous characteristics of stability during use and applicability to standing users, which are best suited for their application to infants who have just started walking.

Conventional tapeless-type articles include pant-type and supporter-type articles. One example of the pant-type article is illustrated in JPA No. 3-82467 wherein a backsheet, formed of an elastic non-woven fabric, covers both of front and rear sections of the diaper. U.S. Pat. No. 4,938,757 discloses a diaper typical to the supporter-type article which includes elastic side bands for connecting side ends of a front section and side ends of a rear section.

When manufacturing, these articles, main bodies of the articles are assembled with their longitudinal direction being arranged either in a machine direction (MD) or in a cross-machine direction (CD), and integrally-formed front and rear sections of each of the main bodies are then bi-folded for side sealing of respective, opposite side ends thereof.

However, such manufacturing methods as mentioned above have certain limitations in terms of productivity and feasibility to accommodate various article constructions. In order to improve the productivity of those articles, JPA No. 3-123551 proposes a method wherein a backsheet is placed on a bi-folded main part comprising a topsheet and an absorbent core placed thereon prior to heat-sealing along wing and leg portions of an article.

It has been recognized that such conventional tapeless-type absorbent articles are unable to fully accommodate various product features sought for more desirable article configurations during use or more gener-specific article specifications. For example, a desirable location of a maximum absorbing capacity is different between diapers for mail and female. In order to meet such needs, an absorbent core is required to have different absorbing capacities, therefore different quantities of absorbent material between opposite sides of a crotch portion of an article.

However, such provision of different quantities of absorbent material between front and rear sides of the absorbent body consequently creates differences in thickness and rigidity between a front side and a rear side of the absorbent body exactly along its center line. When the folding of the absorbent body is not made at a correct position, the topsheet superposed on the absorbent body is also hi-folded at an off-center position so that opposite ends of the topsheet are misaligned to form an irregular waist profile after heat-sealing thereof to the absorbent core. This reduces the product value of the resulting article.

In order to minimize production of such inferior articles, it is required to effect exact alignment of opposite ends of the topsheet when it is bi-folded. It is, however, difficult to hold such flexible material correctly in a desirable position by present commercially available equipment, which results in an increased equipment cost and reduced productivity as well.

It is an object of the present invention to provide a tapeless-absorbent article which is capable of eliminating the above-described disadvantages of conventional tapeless articles that are generally caused by the necessity of bi-folding of absorbent cores.

Another object of the present invention is to provide a method for manufacturing such an improved absorbent article.

SUMMARY OF THE INVENTION

The present invention provides an absorbent article which comprises a main body having a waist hole and a pair of leg holes, an elastic waist portion disposed around the waist hole, and an elastic leg gather disposed around each of the leg holes. The main body comprises a front section and a rear section. The front and rear sections have different constructions from each other and are connected to each other in a crotch regions and side regions of the article. Each of the front and rear sections comprises a backsheet, a topsheet disposed inwardly of the backsheet, and an absorbent body interposed between the topsheet and the backsheet.

Because the absorbent article of the present invention has the front and rear sections which have respective individual constructions formed of respectively selected, desirable materials, the article is capable of accommodating various features so that the front and rear sections are allowed to function substantially independently from each other.

When the absorbent article of the present invention is used as a diaper for infants who frequently lie with their faces down, the front section may comprise a highly absorbent element containing a combination of pulps and super-absorbent materials and the rear section may comprise a thin and expansive absorbent element. This permits front and rear portions of the article to exhibit urine absorbent capacity and capacity of treating fecal material, respectively.

It is preferable that the front section having high absorbing capacities has an overall dimensionally stable construction including an absorbent body and the rear section is provided with elastic materials to be more flexible.

The front section may comprise a topsheet formed of a hydrophobic, bulky, fine-mesh sheet treated to be hydrophilic and the rear section may comprise a topsheet formed of a hydrophilic coarse mesh sheet so that the above-mentioned urine absorbent capacity and the capacity of treating fecal material thereof can be fully exhibited.

Furthermore, the front section may comprise a backsheet formed of a highly liquid-resistant film and the rear section comprises a backsheet formed of a highly air-permeable film so that improved comfort is provided to users during use. Different coloring or patterning of the hacksheet between the front and rear sections permits users to identify the front and rear portions of the absorbent article at a glance.

As described above, the method of assembling the front and rear sections separately from each other and thereafter joining them provides various advantages in designing a variety of absorbent article constructions. However, there exist problems to be solved since the absorbent article has in its crotch region the securement region.

A first problem comes from the securement of the front and rear portions of the absorbent body. The problem needs to be solved by joining them without any defects. A second problem comes from the securement of front and rear portions of the gather. For example, the simple securement of the front and rear portions may disturb continuities thereof. It may prevent the standing leg gathers from standing up in the securement region. Therefore, it becomes important to solve the problem by maintaining continuity of the front and rear standing gather portions.

Now the securement of the front and rear absorbent body portions will be explained. Each of the front and rear sections has a central region including a topsheet, a backsheet and an absorbent body, and a marginal end including the topsheet and the backsheet. The respective marginal ends of the front and rear sections are joined together to form a tab. Those marginal ends may be joined to each other typically by heat-bonding. The heat-bonding may be effected by a plurality of lines or by relatively wide bands to obtain stable securement results. It is preferred that the ends including the absorbent bodies are previously joined to each other by hotmelt adhesives before the marginal ends are heat-bonded to each other. This provides improved, urine leakage protection.

In order to obtain more stable securement, it is advantageous that a reinforcing member is additionally attached to the securement region. One approach is to provide a tape-like reinforcing member along a boundary in a crotch securement region of the front and rear sections. Such a reinforcing member needs to be liquid-permeable and preferably comprises a highly liquid-permeable porous non-woven fabric.

Another effective method is to insert a heat-sealable sheet between the facing top surfaces of the front and rear sections. The heat-sealable sheet is bonded to the front and rear sections simultaneously as they are heat-bonded to form the crotch securement region. In such an event, while one end of the heat-sealable sheet is bonded to the securement region together with the topsheets and backsheets, another end thereof is unsecured to project upwardly like a petal in a central portion of the absorbent article. This projection portion serves to separate the front portion from the rear portion of the article and has an effective function to separate urine from fecal material. Accordingly, the projecting portion may be preferred to as "a separating petal". The separating petal may comprise a heat-sealable film or non-woven fabric, preferably an elastic and heat-sealable elastomeric film or non-woven fabric such as of ethylene vinyl acetate co-polymer (E.V.A.), stylene ethylene butodiene stylene block co-polymer (S.E.B.S.),or stylene ethylene propylene stylene block co-polymer (S.E.P.S.).

Now, the securement of front and rear standing leg gather portions will be explained. As described above, when the front and rear sections are to be joined to form an integral absorbent article, it becomes one of important requirements to maintain the continuities of the gather portions in the crotch securement region. Especially, it is true when the standing gathers are incorporated in the article. The simple securement of the front and rear sections tends to prevent the standing gather portions from standing up in the crotch securement region. Therefore, suitable means needs to be implemented to maintain the continuities of the standing gather portions in the crotch securement region.

According to the present invention, such problems are solved by the following means. Prior to joining the front and rear sections, each of the strip members for forming the standing gather portions is secured at its lower edge to the topsheet by suitable bonding means, with its upper edge being unsecured thereto. Each of the strip members extends longitudinally beyond the absorbent body to define the marginal end together with the backsheet in the crotch securement region. At the stage when the marginal ends of the front and rear sections are joined to each other to form the tab, selected surface areas of the respective strip members of the front and rear sections are placed upon each other. The selected surface area of each strip member extends transversely to its full width and extends longitudinally from the tap portion toward an inner portion of the front or rear section beyond an outer edge of the absorbent body. The selected surface areas of the respective strip members are bonded to each other by hotmelt adhesives.

The triangular bonded portion thus formed between the front and rear sections is referred to as "a cross-over flap" in the specification for convenience of explanation. The cross-over flap formation causes the length dimension of the upper edge of the strip member to be smaller than that of the lower edge of the strip member. This difference in length dimension causes the strip member to stand up from the topsheet to define the so-called standing leg gather.

The formed cross-over flap portion is connected to the topsheet portion through the tab so that it serves to support the standing gather. Accordingly, the cross-over flap portion has the function which effectively prevents the standing gather from moving a great deal inwardly or outwardly; especially from moving outwardly. In the event that the cross-over flap is joined to the aforementioned separator petal, it also serves to maintain the standing leg gather in a substantially upright position. The substantially upright standing gather defines a partition between front and rear portions of the article so that it serves as a separator to prevent urine and fecal material from mixing with each other.

In the present invention, the elasticity of the gather is set to the minimum that permits the inner leg gather to snugly fit to a user's body. As the elasticity increases, the inner leg gather is more likely to yield to the pressure exerted by the movement of the user or by the load of body exudates so that the gather experiences deformation which subsequently cause leakage of the body exudates. Suitable materials for the strip member which forms the inner leg gather include a non-woven fabric having suitable elasticity and flexibility and an elastic composite of a non-woven fabric and an elastic material. A typical example of the elastic non-woven fabric is the one manufactured by subjecting a carded web containing highly heat-shrinkable conjugate fibers of polyesters or polypropylenes to high-pressure water jet and applying heat to the resulting hydroentangled non-woven fabric. Typical examples of the elastic composite include a composite of a non-woven fabric and an elastic film and an composite of a non-woven fabric and elastic meltblown fibers. As will be readily appreciated, the concept of the present invention is also applied to the inner leg gather of conventional construction which includes an elastic material in its head portion and a non-woven fabric in its leg portion.

In accordance with still another aspect of the present invention, there is provided a method for manufacturing an absorbent article which comprises a main body having a waist hole and a pair of leg holes, an elastic waist portion disposed along the waist hole and a leg gather disposed along each of the leg holes. The method comprises the steps of providing a topsheet, an absorbent body and a backsheet for assembling a front section, providing a topsheet, an absorbent body and a backsheet for assembling a rear section, and placing the front section upon the rear section for joining the front and the rear sections to form a crotch region and opposite side regions of the main body.

U.S. Pat. No. 4,427,408 discloses a method for manufacturing the absorbent articles which places a front section upon a rear section for securement thereof. This method however prepares an integral pair of front and rear sections before bi-folding the pair of sections longitudinally or transversely, in contrast to the present method which assembles the front and rear section separately and eliminates the necessity of the bi-folding.

Prior to the placing, step, waist and lea elastics may be provided along peripheries of the waist hole and the lea holes, respectively, to form the waist gather and the leg gathers. A reinforcing step may be added to the above steps to reinforce the crotch securement region.

The present invention further provides a method for manufacturing an absorbent article which comprises a main body having a waist hole and a pair of leg holes, an elastic waist portion disposed along the waist hole and a leg gather disposed along each of the leg holes. The method comprises the steps of providing absorbent bodies in predetermined intervals between a longitudinally moving first continuous web and a longitudinally moving second continuous web to form a first assembly, providing absorbent bodies in predetermined intervals between a longitudinally moving third continuous web and a longitudinally moving fourth continuous web to form a second assembly, moving the first assembly and the second assembly in the same direction for introducing the first assembly upon the second assembly, heat-bonding the first and second assemblies to form the crotch regions and side regions of the main body, and cutting the first, second, third and fourth continuous webs in the heat-bonded regions.

One of the important advantages of the present method is that a step of bi-folding a member including a topsheet, a backsheet and an absorbent body in a crotch region is eliminated because a front section and a rear section of an absorbent article are separately assembled before they are joined to each other in a crotch region and opposite side regions. Therefore, the present method is capable of eliminating the troublesome alignment of the front and rear sections necessitated by the bi-folding to provide improved process efficiency and a reduced rate of product loss.

BRIEF DESCRIPTION OF THE DRAWINGS

FIGS. 21A, 211B, 21C illustrate a portion of the absorbent article of FIG. 20 wherein 21A is a partly cut-away perspective view illustrating a leg gather portion, 21B is a view illustrating a tab portion formed in the leg gather portion and 21C is a view illustrating an angle at which the leg gather stands up;

DETAILED DESCRIPTION OF THE PREFERRED EMBODIMENTS

Figure 1:
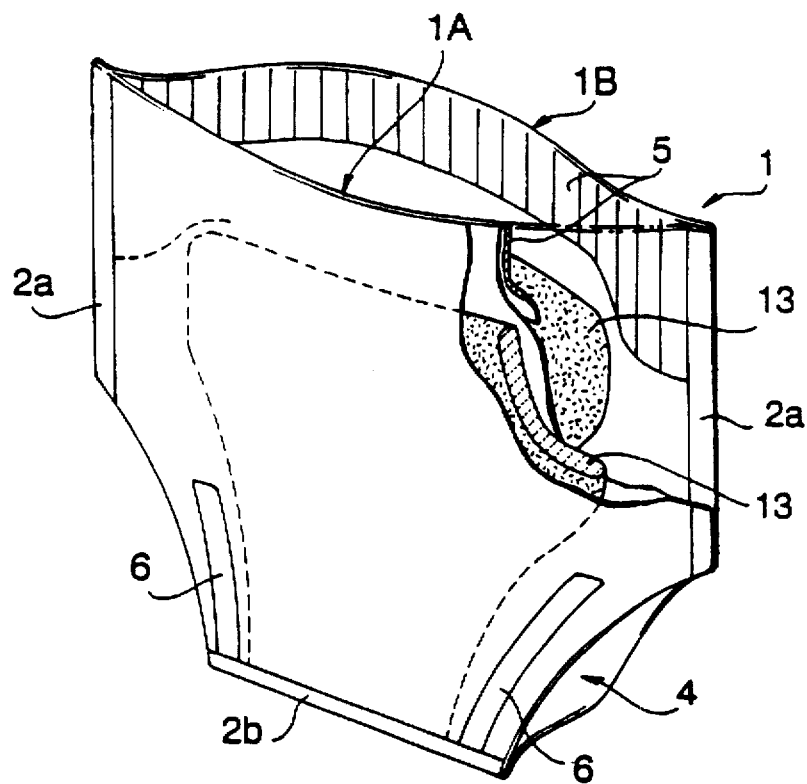
FIG. 1 is a perspective view of a first embodiment of an absorbent article in accordance with the present invention, partially cut away to reveal the inside structure.
Figure 2:
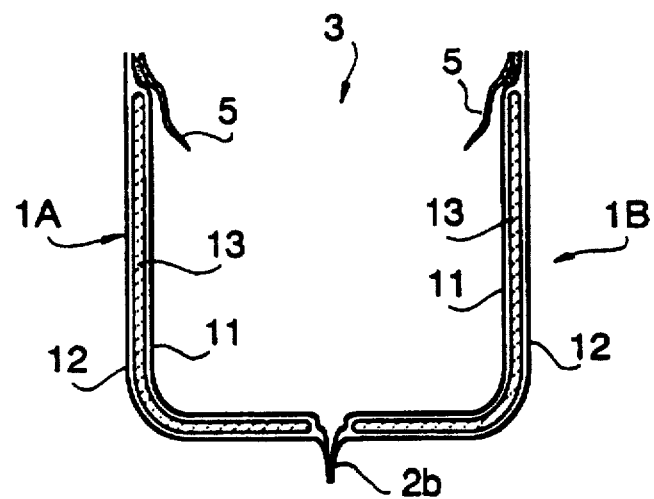
FIG. 2 is a longitudinal cross-section view of the absorbent article of FIG. 1.
Figure 3:
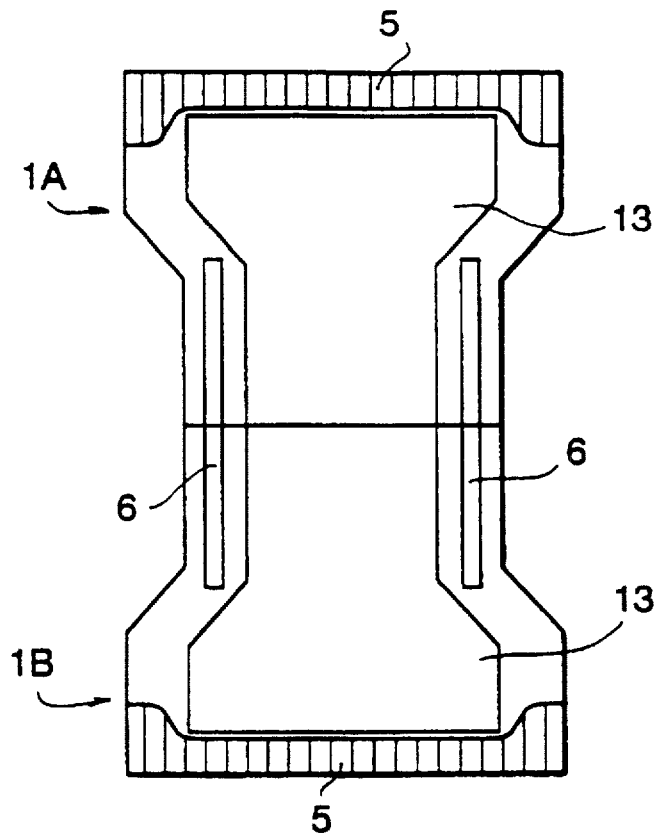
FIG. 3 is a developed plan view of the absorbent article of FIG. 1 with a topsheet removed.

FIGS. 1 through 3 illustrate one embodiment of a tapeless absorbent article in accordance with the present invention In the drawings, reference numeral 1 indicates a main body which comprises a front section 1A and a rear section 1B. These sections are joined to each other by suitable bonding means such as heat-bonding to form side securement regions 2a in opposite side regions of the article and in a crotch securement region 2b in a crotch region of the article. The main body 1 includes a waist hole 3 and a pair of leg holes 4. An elastic waist gather 5 is disposed along the periphery of the waist hole 3. An elastic leg gather 6 is disposed along the periphery of each of the leg holes 4.

As illustrated in FIG. 2, each of the front section 1A and the rear section 1B each comprises a topsheet 11 formed of liquid permeable and hydrophobic material, i.e. a hydrophobic non-woven fabric, a backsheet 12 formed of liquid impermeable material, and an absorbent body 13 interposed between the topsheet 11 and the backsheet 12.

It is to be understood that the topsheets 11, the backsheets 12 and the absorbent bodies 13 are separately disposed, respectively, between a boundary between the front section 1A and the rear section 1B. The front section 1A and the rear section 1B are independent from each other until they are integrally joined to each other in securement regions 2a, 2b.

The absorbent article of such structure includes the main body 1 constructed by joining the initially separate, front and rear sections 1A, 1B in the securement regions 2a, 2b. Therefore, it becomes possible that the front section 1A and the rear section 1B may use different materials for any of their respective topsheets 11, backsheet 12 and absorbent bodies 13. This permits the front and rear sections 1A, 1B to function differently or individually.

In a particular embodiment, the absorbent body 13 of the front section 1A comprises a highly absorbent element containing, a combination of pulps and super absorbent materials generally referred to as "SAP" and the absorbent body 13 of the rear section 1B comprises a thin and expansive absorbent element, so that the front and rear sections can serve as a urine spot and a fecal spot, respectively.

It is possible to exhibit an optimum urine absorbent capacity and the capacity of treating fecal material thereof as mentioned above, when a topsheet of a hydrophobic fine-mesh sheet treated to be hydrophilic is used for the front section 1A, and a topsheet formed of a hydrophilic coarse mesh sheet is used for the rear section 1B.

Figure 4:
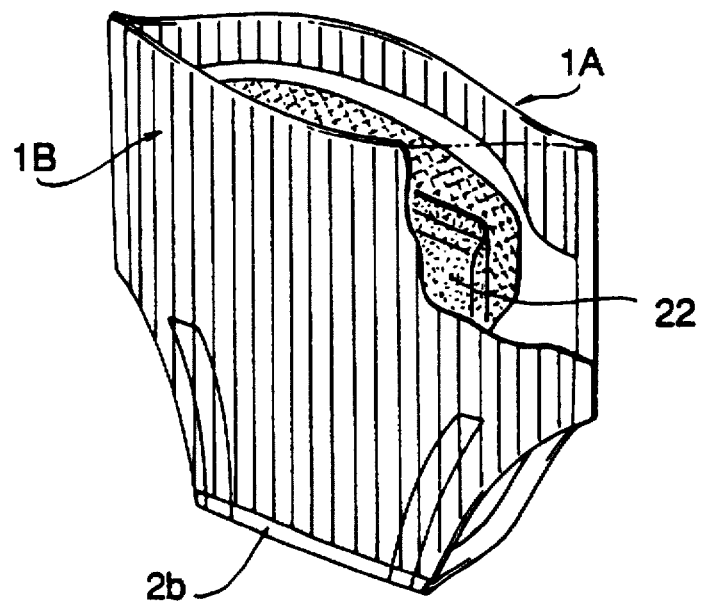
FIG. 4 is a partially cut-away perspective view of a second embodiment of an absorbent article in accordance with the present invention.
Figure 5:
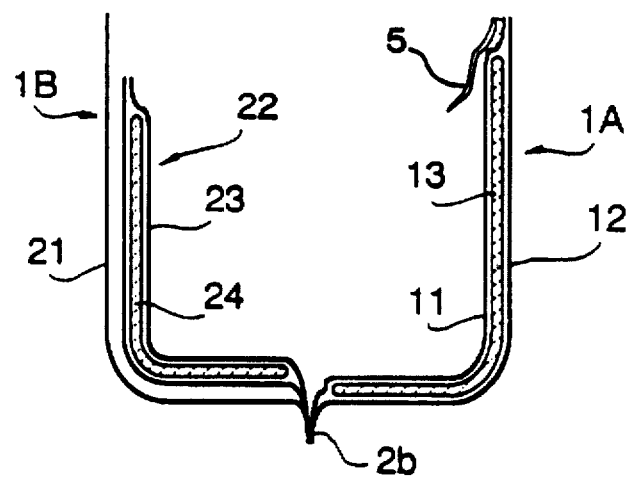
FIG. 5 is a longitudinal cross-sectional view of the absorbent article of FIG. 4.
Figure 6:
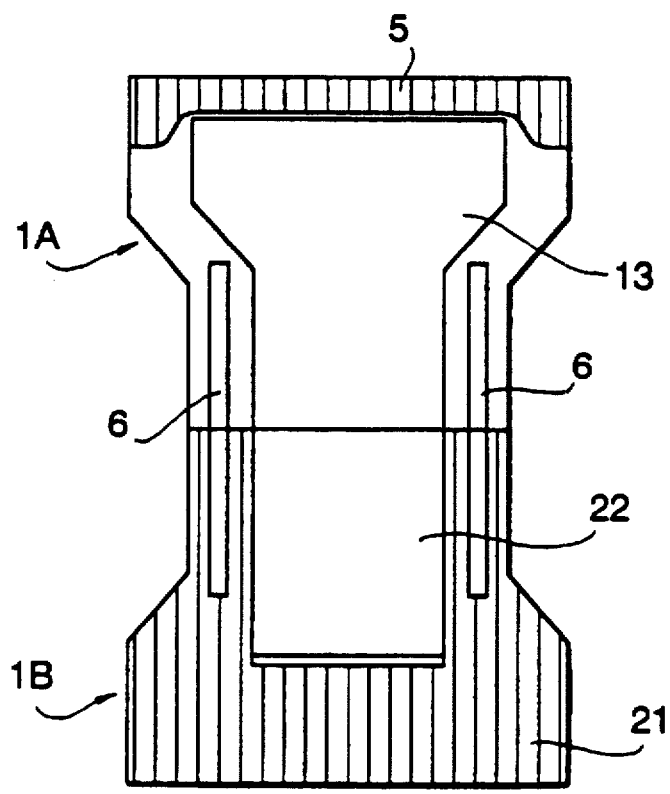
FIG. 6 is a developed plan view of the absorbent article of FIG. 4 with a topsheet removed.

FIGS. 4 through 6 illustrate a second embodiment of the absorbent article in accordance with the present invention. The absorbent article includes a front section 1A as constructed similarly to the front section of FIGS. 1 through 3, and a rear section 1B which comprises an elastic composite sheet 21, as will be hereinafter described, and an absorbent pad 22 disposed inwardly of the composite sheet. As illustrated in FIG. 5, the absorbent pad 22 is rectangularly configured and is sealed at its peripheries to enclose an absorbent core 24 within a pouch-like cover 23. The absorbent pad 22 is at its one periphery joined to the elastic composite sheet 21 by suitable means such as heat-bonding. The same reference numerals are used throughout FIGS. 1 through 6 to indicate the same or similar elements to minimize redundancy in the explanation thereof.

Figure 7:
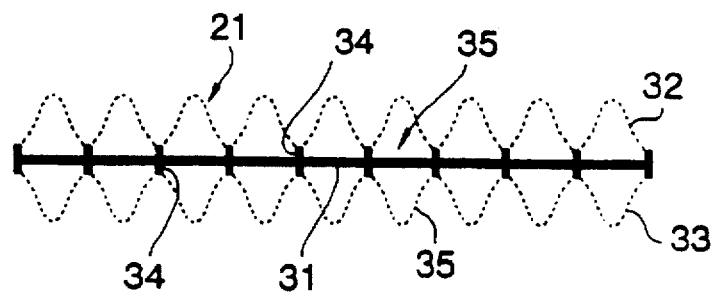
FIG. 7 is a fragmentary longitudinal cross-sectional view of an elastic composite sheet suitable for use in an absorbent article of the present invention.

The elastic composite sheet 21 as is employed to construct the rear section 1B is illustrated in FIG. 7. The elastic composite sheet comprises a heat-sealable, film or non-woven elastic sheet 31 formed of synthetic rubber, polyurethane, styrene-butadiene block polymer or polyolefin elastomers, and a non-woven fabric 32, 33 heat-bonded to at least one surface (to both surfaces in the illustrated embodiment) of the elastic sheet 31 by a plurality of parallel securement lines 34. The non-woven fabric, 32, 33 provides soft touch to a human skin Preferably, the elastic composite sheet includes a plurality of channel-like spaces 35 defined between the elastic sheet 31 and the non-woven fabric 32, 33.

The absorbent article of such construction can be smoothly applied to and removed from a human body since its rear section 1B comprises the highly elastic composite sheet 21, and is capable of snugly fitting to any human body profiles and of following any movements of the human body so that it provides better comfort to users during use.

FIGS. 8 through 11 illustrate a third embodiment of the present absorbent article. In the illustrated embodiment, side panels 41a are connected to a front section 1A to respectively extend from opposite side ends of the front section 1A. Likewise, side panels 41b are connected to a rear section 1B to respectively extend from opposite side ends of the rear section 1B. The elastic composite sheet is dually layered to form each of the side panels. Leading ends of the side panels 41a are joined to respective leading ends of the side panels 41b to connect the front section 1A and the rear section 1B.

A waist elastic 5 is interposed between the topsheet 11 and the backsheet 12 to form a waist gather disposed along a waist hole 3. A leg elastic 6 is attached to each of the side panels 41a, 41b.

Because side panels 41a, 41b are elastically stretchable and contractable, they are capable of elastically cooperating with the elastic waist portion disposed along the waist hole to facilitate application and removal of the article and provide improved fit thereof to the human body during application.

Figure 12:
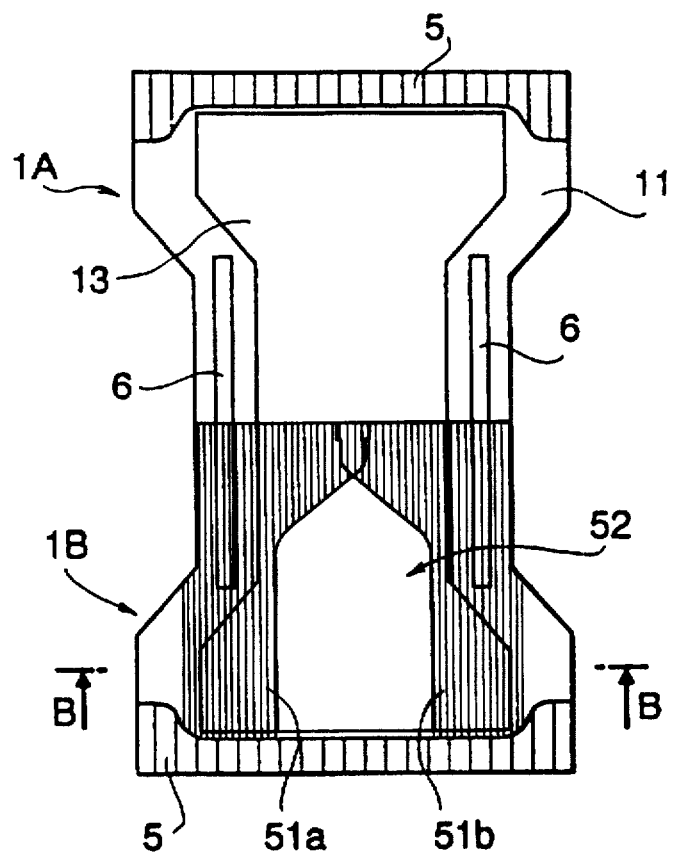
FIG. 12 is a developed plan view of a fourth embodiment of an absorbent article of the present invention with a topsheet removed.
Figure 13:
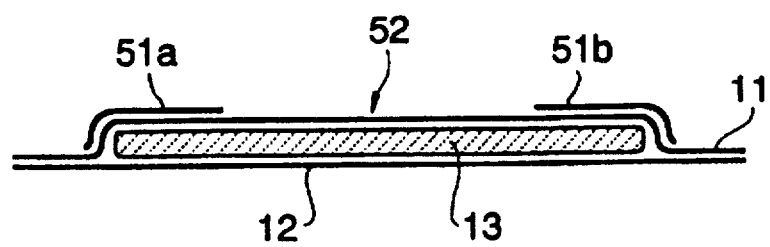
FIG. 13 is an enlarged cross-sectional view taken along a line B—B of FIG. 12.

FIGS. 12 and 13 show a fourth embodiment of the present absorbent article. In this embodiment, a front section 1A is assembled similarly to the first embodiment as illustrated in FIG. 3 to comprise a backsheet 12, a topsheet 11, an absorbent body 13, a waist gather 5 and leg gathers 6. In addition to such elements, a rear section 1B further includes cuff barriers 51a, 51b. These cuff barriers 51a, 51b may comprise the elastic composite sheet as illustrated in FIG. 7. Each of the cuff barriers 51a, 51b extends laterally from a side edge of the rear section 1B toward a center of the rear section to cover the topsheet 11 of the rear section 1B. Leading ends of the cuff barriers are respectively contoured to define an opening 52 therebetween. Accordingly, the topsheet 11 and the cuff barriers 51a, 51b of the rear section 1B define therebetween a pocket communicating with outside through the opening 52 for containment of fecal material.

Figure 14:
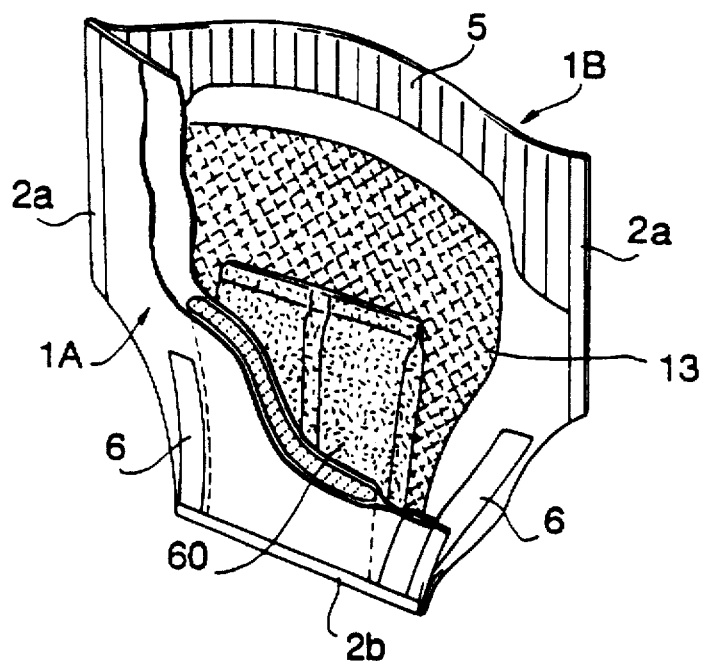
FIG. 14 is a partly cut-away perspective view of a fifth embodiment of an absorbent article in accordance with the present invention.
Figure 15:
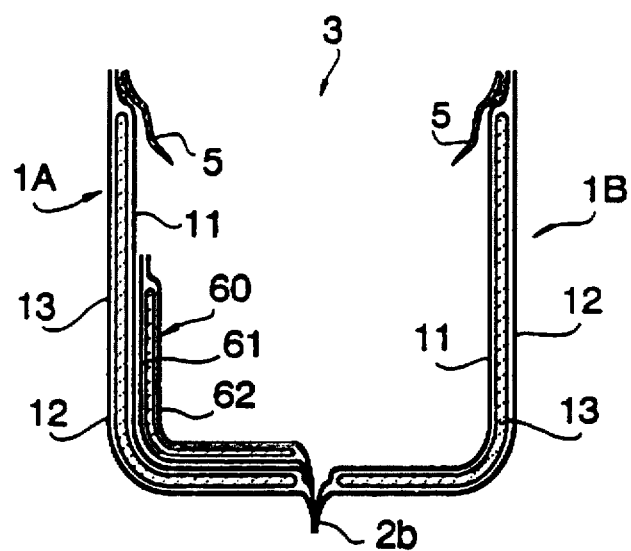
FIG. 15 is a longitudinal cross-sectional view of the absorbent article of FIG. 14.
Figure 16:
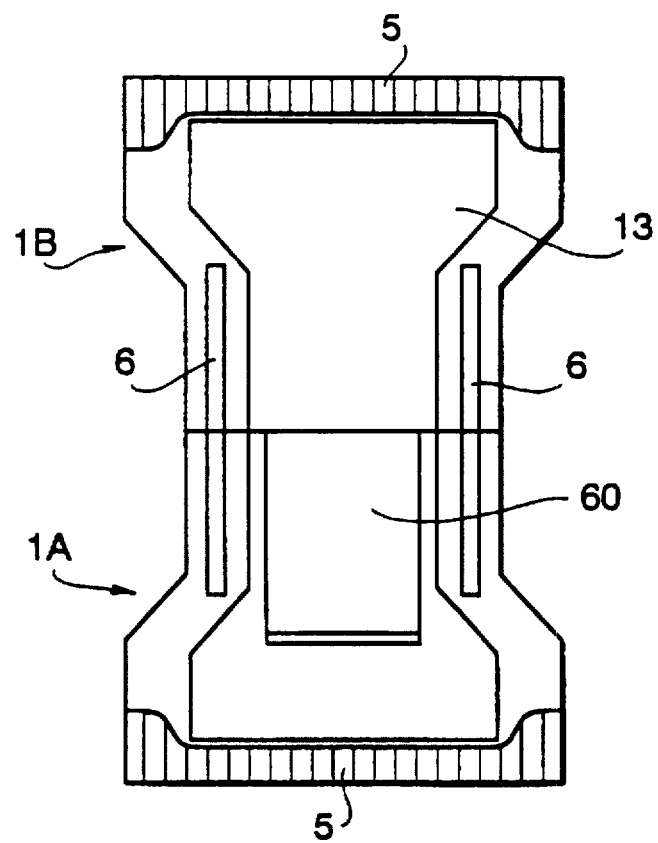
FIG. 16 is a developed plan view of the absorbent article of FIG. 14 with a topsheet removed.

FIGS. 14 through 16 illustrate a fifth embodiment of the absorbent article in accordance with the present invention. In this embodiment, a front section 1A and a rear section 1B may be respectively assembled similarly to those of the first embodiment of FIG. 3 to respectively include a backsheet 12, a topsheet 11, an absorbent body 13, a waist gather 5 and a leg slather 6. In addition, an absorbent pad 60 of relatively small size is attached to the securement region of the front and rear sections 1A, 1B. The absorbent pad 60 comprises a liquid permeable, rectangularly shaped pouch-like cover 61 and an absorbent core 62 enclosed in the cover 61, and is at its one end joined to the securement region of the front and rear sections 1A, 1B.

In FIG. 15, the absorbent pad 60 is illustrated to sit on the topsheet 11 of the front section 1A. This configuration helps exhibit absorbent characteristics particularly suitable for diapers for males. The absorbent pad 60 may be moved to sit on the rear section 1B to provide another configuration more suitable for diapers for females.

As described above, one of the important features of the present invention is that separately assembled front and rear sections are joined to each other in a crotch region and side regions of the article. Generally, the crotch region of the absorbent article is a spot for receiving a majority of body exudates during a normal use thereof. Therefore, an absorbent capacity and a liquid-sealing characteristics of the article in the crotch region is one of the critical factors in determining performance of the absorbent article. Since the securement region of the front and rear sections 1A, 1B is located in the crotch region of the present absorbent article, it is important to assure sufficient liquid-sealability of the article in the crotch region.

The absorbent article suitable for actual use may be obtained when heat-sealable materials are used to form a topsheet and a backsheet. However, in the event that materials for use are difficult for conventional bonding means to effect liquid-tight sealing thereto, or in the event that absorbent articles for certain use require more highly liquid-tight crotch construction, particular designs may be employed to join the front and rear sections to form the crotch region.

Figure 17A:
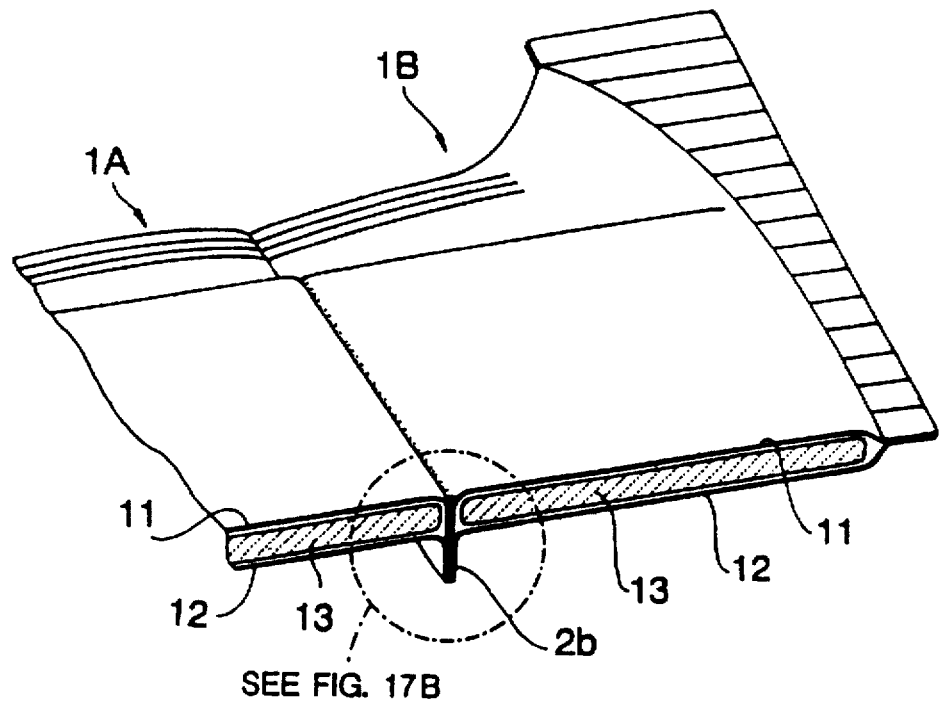
FIG. 17A is a partly cut-away perspective view with a magnified section 17B illustrating a preferred embodiment of a joint construction between a front section and a rear section.
Figure 17B:
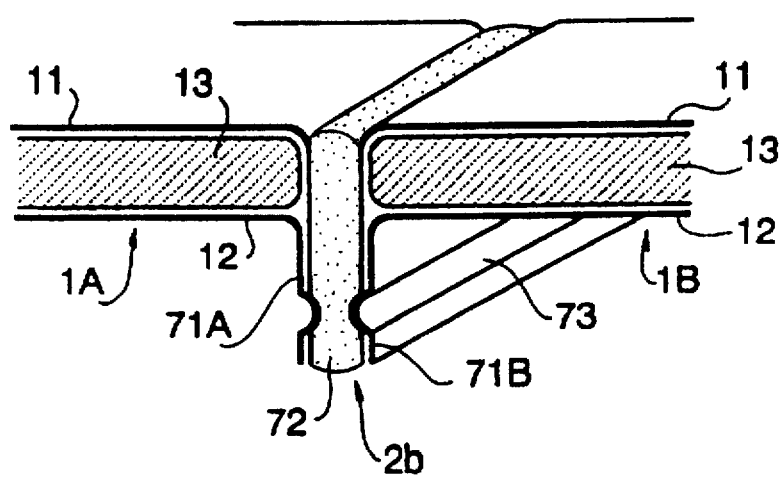

FIG. 17 shows a particular joint construction which provides a highly liquid-tight crotch region of an absorbent article. In FIG. 17, a topsheet 11 and a backsheet 12 of a front section 1A of the article are at their respective crotch ends placed upon each other to define a tab 71A. Similarly, a topsheet 11 and a backsheet 12 of a rear section 1B of the article are at their respective crotch ends placed upon each other to define a tab 71B. Those tabs 71A, 71B are first positioned in a confronting relationship, with hotmelt adhesives 72 being carried on the confronting faces thereof, and then heat-bonded to each other by a securement line 73. Such a joint construction provides highly liquid-tight characteristics at a boundary between the front section 1A and the rear section 1B so that liquid leakage is prevented under any use conditions of the article.

Figure 18A:
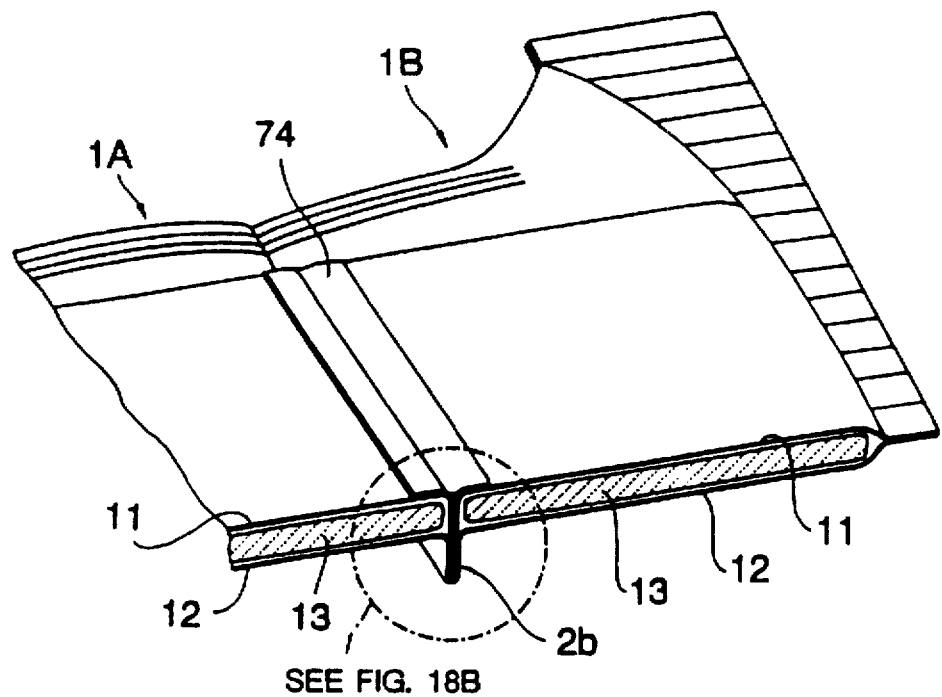
FIG. 18A is a partly cut-away perspective view with a magnified section 18B illustrating another preferred embodiment of a joint construction between a front section and a rear section.
Figure 18B:
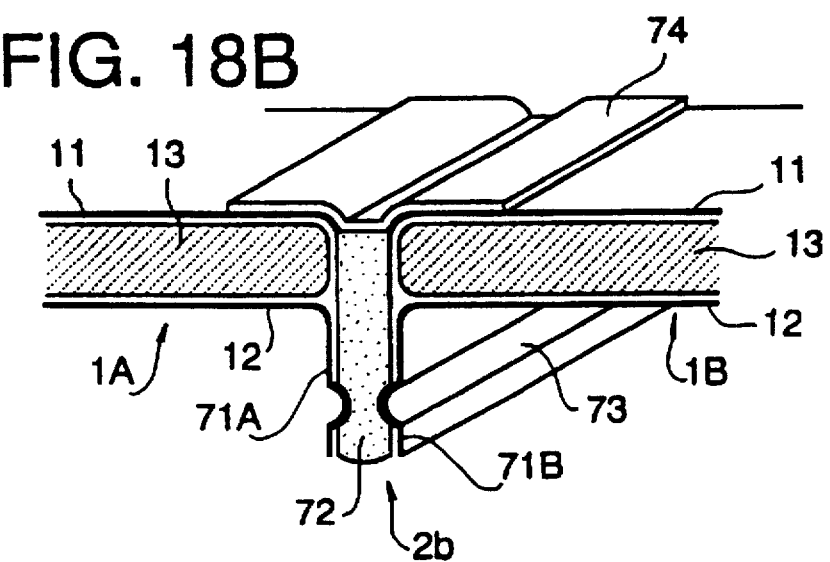

As illustrated in FIG. 18, a reinforcing member 74 may be additionally provided and secured along a boundary line between the front section 1A and the rear section 1B to provide improved leakage protection and improved strength against tearing.

Figure 19A:
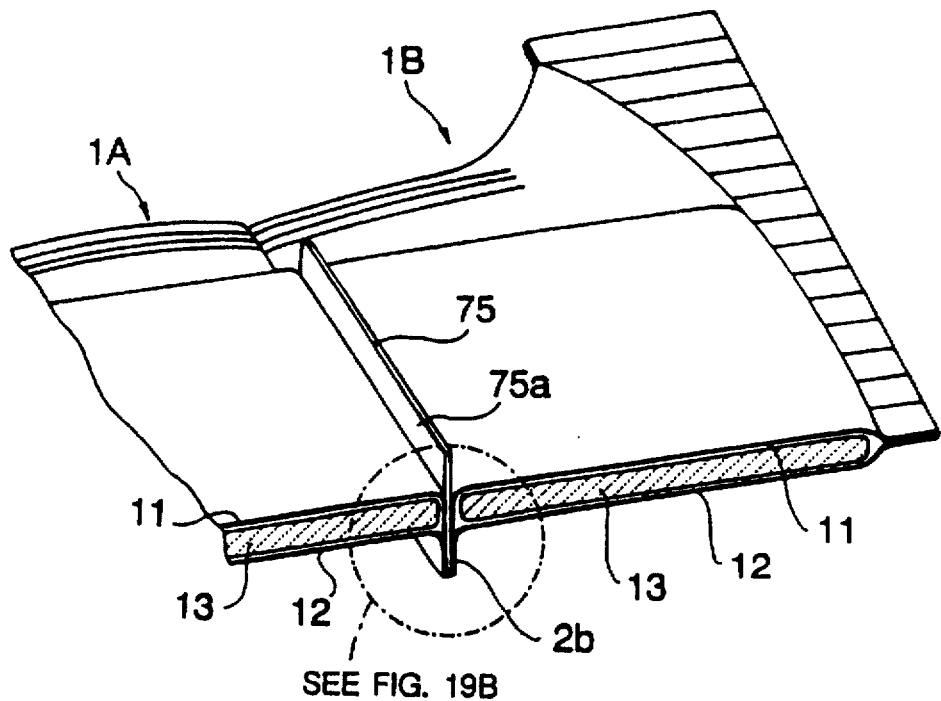
FIG. 19A is a partly cut-away perspective view with a magnified section 19B illustrating still another preferred embodiment of a joint construction between a front section and a rear section.
Figure 19B:
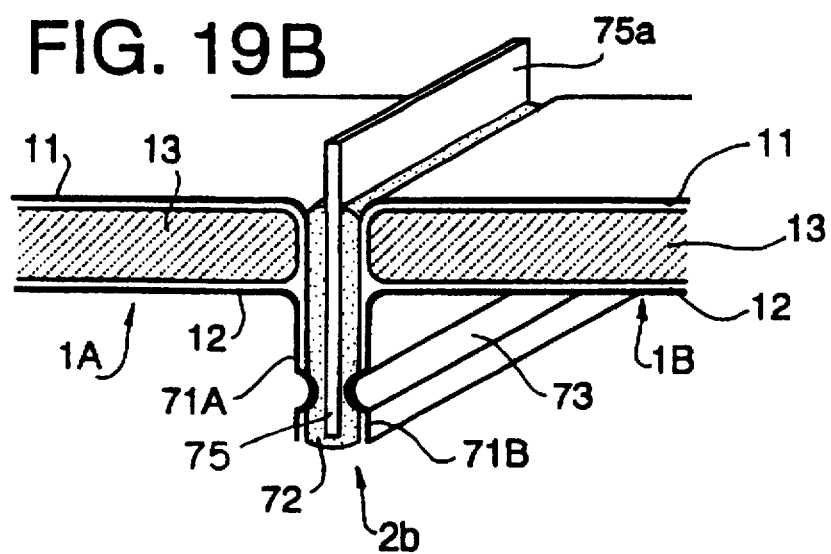
Figure 20:
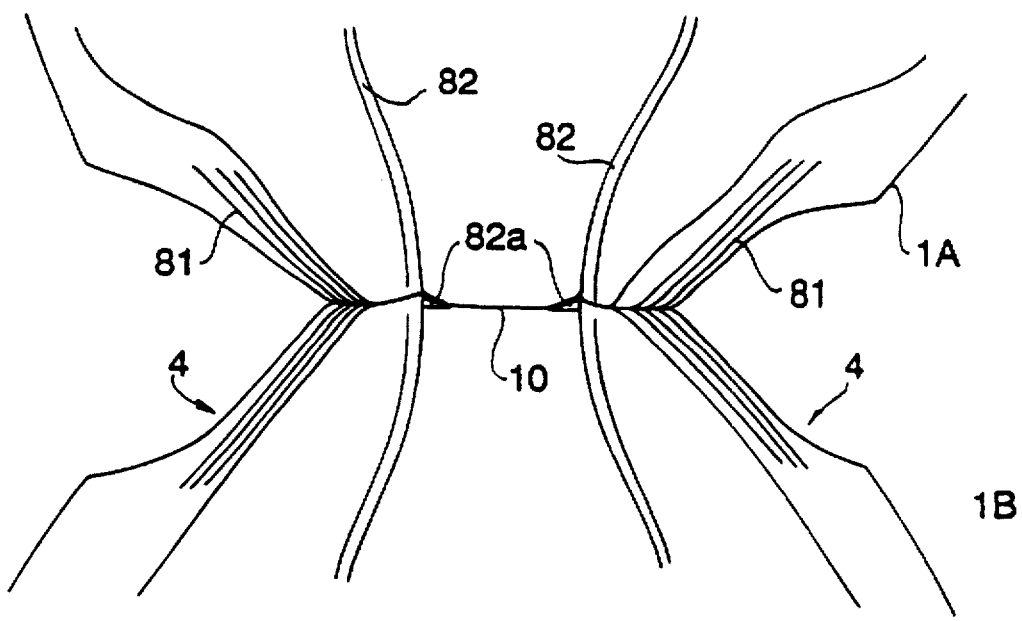
FIG. 20 is a partly cut-away perspective view of still another embodiment of an absorbent article in accordance with the present invention.

FIG. 19 shows an alternative embodiment of the joint construction of FIG. 17 which also provides a highly liquid tight property. In FIG. 19, the tabs 71A, 71B are faced toward each other with a separator 75 therebetween. The separator 75 may be formed of a flexible film, preferably of a heat-sealable film or non-woven fabric. The separator 75 is interposed between and heat-bonded to the tabs 71A, 71B carrying adhesives 72 such as hotmelts by a securement line 73. An end portion of the separator extends upwardly from the topsheet 11 to define a projection 75a. The projection 75a partitions the article into front and rear portions and serves as a separating petal which functions to effectively separate urine from fecal material as described above.

As will be readily appreciated, any materials or any combinations of constructions enabling the front section 1A and the rear section 1B to function individually as illustrated in the above embodiments are merely exemplary and can be optionally selected in accordance with requirements by varieties of usages or applications.

Furthermore, when the backsheets of front and rear sections are respectively formed of films with different colors or patterns, it becomes easy for users to identify the front and rear portions of the article at a glance.

FIGS. 20 through 23 show an absorbent article of the present invention which includes leg gathers. Similarly to the above embodiments, the article includes a main body comprising a front section 1A and a rear section 1B which are joined to each other by tabs 2b. In this embodiment, the article has first gathers 81 each comprising an elastic strip member and second gathers 82 each disposed inwardly of the respective first gather and comprising a strip member.

The first gathers 81 and the second gathers 82 respectively extend along the leg hole 4 of the article. For convenience, the first gathers and the second gathers are hereinafter referred to as outer leg gathers and inner leg gathers, respectively. The outer leg gathers 81 can be optionally omitted. In such an event, the inner leg gathers also serve as the outer leg gathers.

Each of the inner leg gathers 82 comprises a strip member formed of suitably flexible material and extends longitudinally across a crotch region of the absorbent article. The inner leg gathers 82 are laterally spaced from each other a predetermined distance to define a containment zone therebetween for absorbing or holding exudates therein. The strip member is at its one side end joined to an exposed surface of the topsheet 12 to form each of the inner leg gathers 82.

In accordance with one important feature of the present invention, each of the inner leg gathers 82 stands up from the topsheet II of the main body I at a suitable angle during use of the absorbent article. In the following embodiments, the standing feature of the inner leg gather 82 is effected by shortenings the length dimension of a second end (hereinafter referred to as "a distal end") remote from the topsheet 11 with respect to the length dimension of a first end (hereinafter referred to as "a proximal end") joined to the topsheet 11.

Figure 21A:
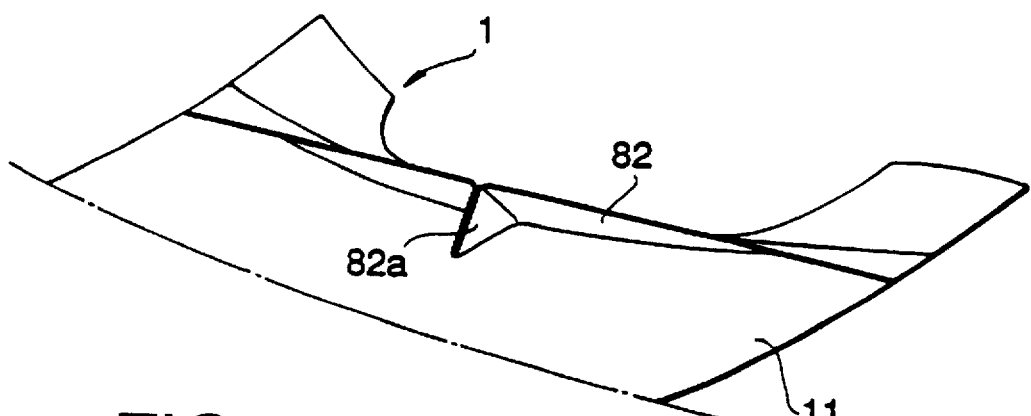
Figure 21B:
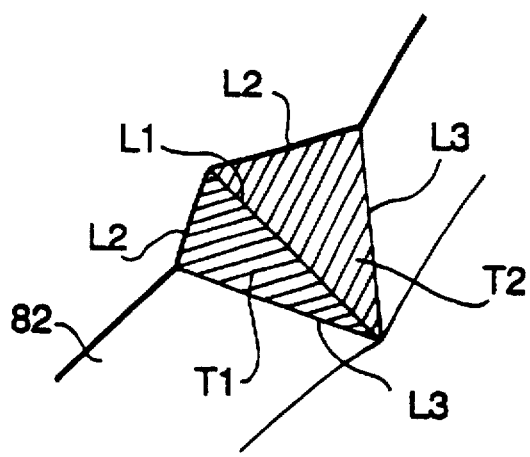
Figure 21C:
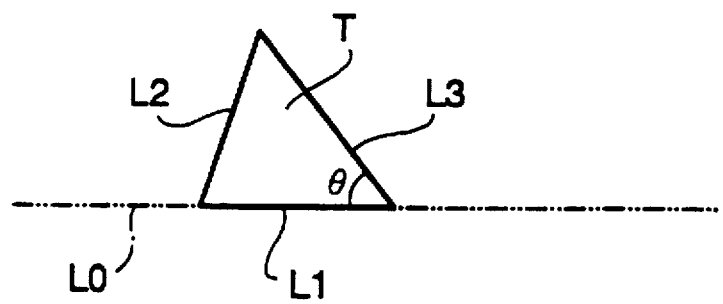
Figure 23A:
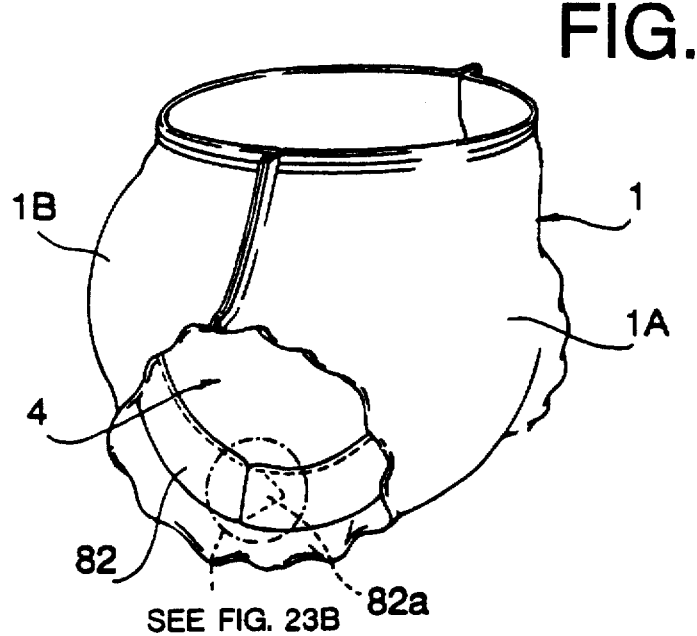
FIG. 23 is a perspective view with a magnified section of still another preferred embodiment of a joint construction of a front section and a rear section.
Figure 23B:
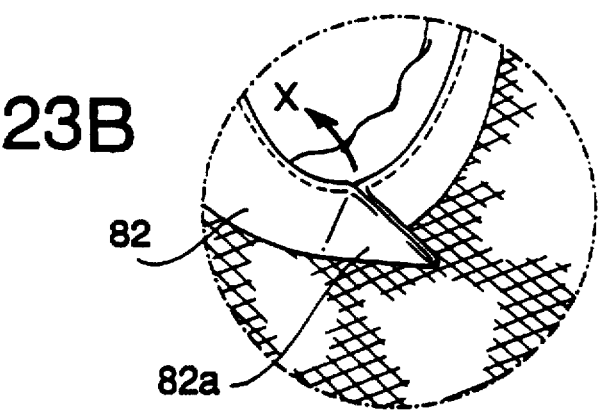

In a particular embodiment as illustrated in FIGS. 21A, 21B, 21C, the inner leg gather 82 is tucked in the crotch region of the main body I along folding lines which extends divergently and upwardly from the proximal end toward the distal end and for securement so that a cross-over flap 82a of substantially triangular shape is formed.

While the secured cross-over flap 82a may be formed by tucking the inner leg gather either inwardly or outwardly, it is preferred from view points of product appearances and its other utilities to tuck the inner leg gather inwardly so that the cross-over flap extends inwardly therefrom.

The extent of the inclination of the gather 82 is selectively determined by the extent of shortening of the distal and with respect to the proximal end of the strip member. Referring to FIG. 21B, three folding lines are formed to extend upwardly from the proximal end toward the distal end of the strip member. The outer and inner folding lines extend upwardly in a diverging relationship toward each other so that two triangles T1, T2 are defined. These two triangles T1, T2 are defined to be symmetrical with respect to the intermediate folding line L1. Each of the triangles T1, T2 includes the folding line L1 which bounds the two triangles, a line L2 which extends along the distal end of the strip member, and a folding line L3 which traverses the strip member at a suitable angle with respect to the folding line. These two triangles are placed upon each other for securement to form the cross-over flap 82a as above mentioned.

FIG. 21C shows a triangle T defined by the cross-over flap 82a. In FIG. 21C, reference numeral L0 indicates a base line which corresponds to a top surface of the topsheet 11 to which the cross-over flap 82a is attached. The line L3 of the triangle T defined by the cross-over flap 82a is inclined by a predetermined angle θ with respect to the base line topsheet) L0. The angle θ of inclination becomes greater as the length dimension of the line L2 of the triangle T increases. As the angle becomes greater, a top of the cross-over flap 82a is further spaced away from the topsheet 11 and is moved further upwardly.

Figure 22:
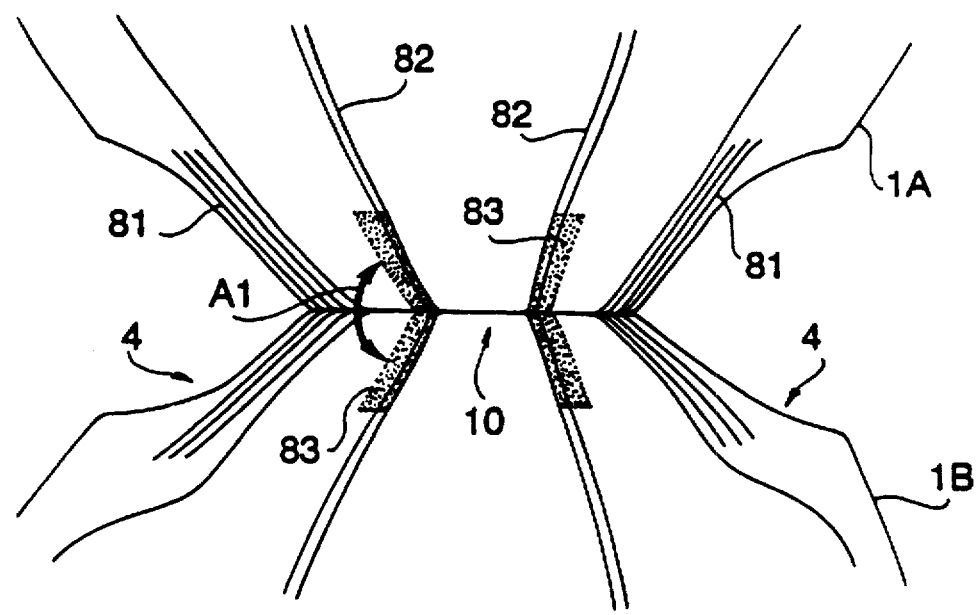
FIG. 22 is a partly cut-away perspective view of the absorbent article shown in FIG. 20 as being in the state before secured.

Although it is not required that the cross-over flap 82a of substantially triangular shape is secured to any other members, it may be secured to the topsheet 11 inwardly of the inner leg gather 82. FIG. 22 shows one embodiment of the absorbent article during use which incorporates the cross-over flap therein. By this construction, the crossover flap 82a acts to pull the inner leg gather 82 inwardly in the crotch region against the force (shown by an arrow X in the drawing of FIG. 23) exerted by the leg action of a user which acts to pull out the inner leg. gather 82 from the leg hole 4. Therefore, the provision of the cross-over flap serves to prevent such an inconvenience from taking place when the construction is applied to the tapeless absorbent article wherein the user inserts a leg into a leg hole 4 from inside of the article.

In an actual production of the absorbent article of the present invention, it is possible to use the procedure set out below. As illustrated in FIG. 22, in a stage prior to securement of the front and rear sections 1A and 1B together at a joint portion 10, the strip members for forming the inner leg gathers 82 are connected at their lower edges to the topsheets 11, respectively. Layers 83 of an adhesive material such as of hot-melt-type are applied on the side facing, together of each pair of the strip members over a suitable length. The topsheets 11 of the front and rear sections 1A and 1B are then forced to contact to each other in the direction of an arrow A1, thereby to bond the strip member pairs by the adhesive layers 83.

As a result, each pair of the strip members are connected together to form the continuous leg gather pair 82. Each of the leg gathers 82 thus formed is connected to the topsheet 11 at its lower edge, and at the joint portion 10 the upper edge is also connected to the topsheet. In this construction, the upper edge of each leg gather is longer than the lower edge, thereby to stand up the leg gather when the absorbent article is applied to the wearer's body.

Figure 24:
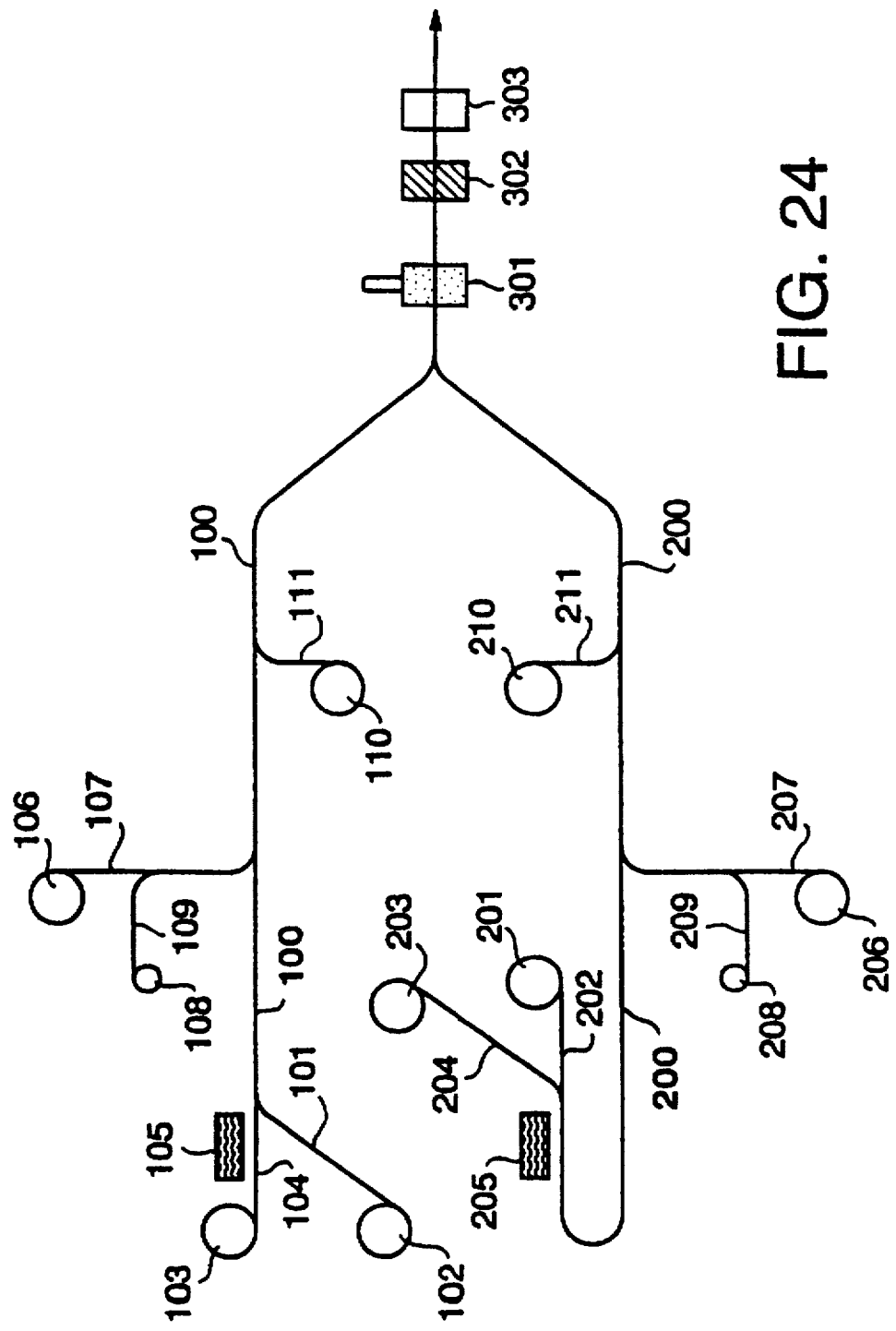
FIG. 24 is a schematic flow diagram illustrating an exemplary process for manufacturing the first embodiment of the absorbent article in accordance with the present invention.

Now the explanation is made with reference to FIG. 24 regarding one exemplary method of manufacturing absorbent articles as illustrated in FIGS. 1 through 3. In accordance with this method, a first step of assembling the front section is performed simultaneously with a second step of assembling the rear section. The subsequent third step involves joining the individually assembled front and rear sections.

First, the first step which assembles the front section will be explained. Referring to FIG. 24, a first sheet 101 comprising a continuous web is continuously withdrawn from a roll 102 at a predetermined constant speed. Meanwhile, a carrier sheet 104 is continuously withdrawn from a roll 103. A pulp former 105 treats absorbent materials such as pulp to feed preformed absorbent bodies (not shown) of predetermined shape to place them onto the carrier sheet 104 at predetermined intervals. The first sheet 101 is then placed upon the carrier sheet 104 carrying the absorbent bodies to form a first assembly 100.

An elastic leg material 109 withdrawn from a roll 108 is attached to a second sheet 107 which is in turn withdrawn from a roll 106 by bonding means which is not shown in the drawing. The second sheet 107 carrying the elastic lee material is subsequently placed upon the first sheet 101 and the absorbent bodies. A waist gather material 111 withdrawn from a roll 110 is placed on a bottom side of the first sheet 101 which is then transferred to a next step.

The second step of assembling the rear section is performed likewise the first step. A second sheet 201 comprising a continuous web is continuously withdrawn from a roll 202 at a predetermined constant speed. Meanwhile, a carrier sheet 204 is continuously withdrawn from a roll 203. A pulp former 205 treats absorbent materials such as pulp to feed preformed absorbent bodies (not shown) of predetermined shape to place them onto the carrier sheet 204 at predetermined intervals. The second sheet 201 is then placed upon the carrier sheet 204 carrying the absorbent bodies to form a second assembly 200.

An elastic leg material 209 withdrawn from a roll 208 is attached to a second sheet 207 which is in turn withdrawn from a roll 206 by bonding means which is not shown in the drawing. The second sheet 207 carrying the elastic leg material is subsequently placed upon the second sheet 201 and the absorbent bodies. A waist gather material 211 withdrawn from a roll 210 is placed on a bottom side of the second sheet 201 which is then transferred to a next step. However, the positional relationship of the second sheet 201, the carrier sheet 204, the absorbent body and the waist gather material 211 is reversed from that of the first assembly with respect to the first sheet 101.

In the above embodiment, the first sheet 101 comprises a non-woven fabric which forms a topsheet and the second sheet 201 comprises a liquid impermeable film which forms a backsheet.

The first assembly 100 and the second assembly 200 as manufactured via the above steps are then placed upon each other so that the absorbent bodies thereon face toward each other, and are subsequently introduced into a supersonic sealing equipment 301 where they are heat-bonded to each other along, a crotch region and side regions of the resulting article. It is important in this step to assure that the first assembly 100 and the second assembly 200 are correctly aligned with each other. This alignment can be readily effected by synchronizing the feed speeds of the assemblies 100, 200.

After the heat-bonding is completed, cutting is effected by a round cutter 302 to form the leg holes, and subsequent cutting by an end cutter 303 separates the bonded assemblies into individual article pieces.

Figure 8:
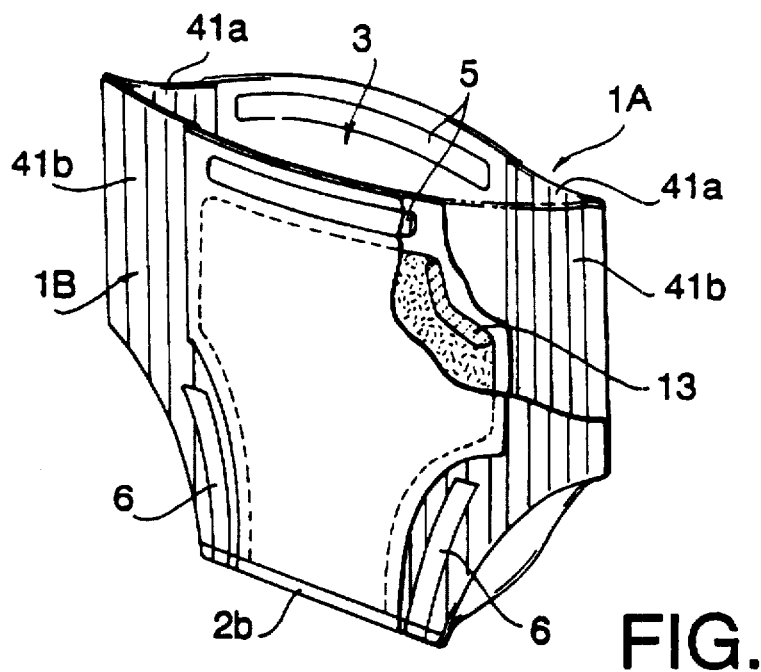
FIG. 8 is a partly cut-away perspective view of a third embodiment of an absorbent article in accordance with the present invention.
Figure 9:
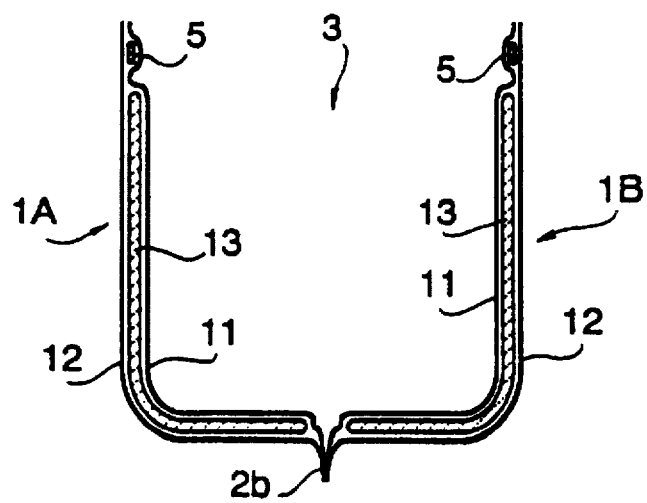
FIG. 9 is a longitudinal cross-sectional view of the absorbent article of FIG. 8.
Figure 10:
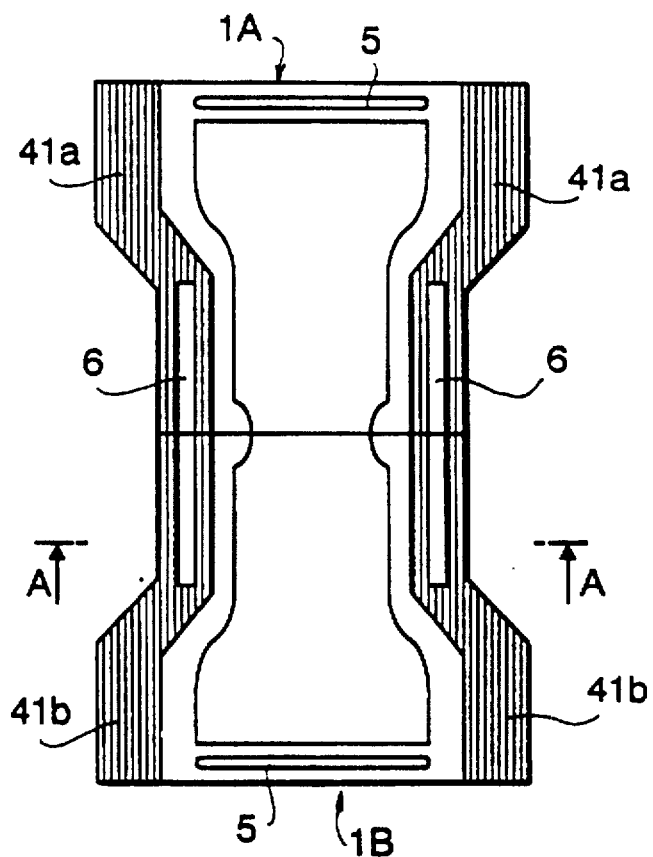
FIG. 10 is a developed plan view of the absorbent article of FIG. 8 with a topsheet removed.
Figure 11:
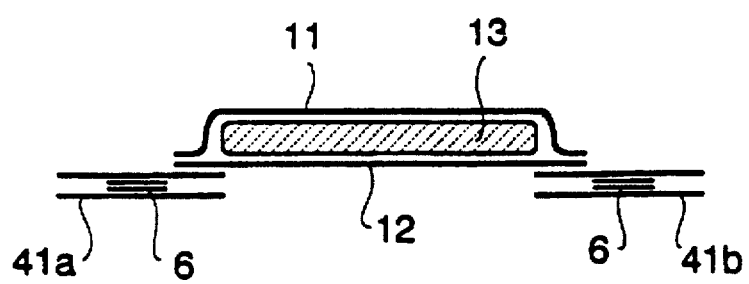
FIG. 11 is an enlarged cross-sectional view taken along a line A—A of FIG. 10.

In order to manufacture the absorbent article as illustrated in FIG. 8 which joins the respective side ends of the front and rear sections by the elastic side panels 41a, 41b, the elastic strip members comprising those side panels 41a, 41b may be previously attached to opposite side ends of each of the first and second sheets 1A, 1B such as by heat-bonding before distal ends of the respective strip members are heat-bonded to each other by the supersonic sealing equipment 301.

Alternatively, the elastic waist portion 5 may be dimensioned so that its opposite side ends extend outwardly from respective side edges of each of the front and rear sections to define the side panels 41a, 41b.

As described above, the absorbent article in accordance with the present invention comprises the front and rear sections which include individual topsheets, backsheets and absorbent bodies, and are joined to each other by suitable bonding means such as heat-bonding at a crotch region and opposite side regions of the absorbent article. This permits the front and rear portions of the absorbent article to function differently from each other so that the present absorbent articles are able to be responsive to various needs including various configurations for use.

Furthermore, in accordance with the present method, the front and rear sections are separately assembled before they are finally bonded to each other to form a final product. Therefore, the present method is able to eliminate the conventional folding step in which the topsheet and absorbent body assembly are folded along a crotch region, and accordingly to eliminate necessity of the troublesome alignment of side ends thereof during the folding step. As a result, the present method provides a greatly reduced rate of product loss and facilitates an overall process control.

We claim:

1. An absorbent article comprising:

a main body having a waist hole and a pair of leg holes, a crotch region between the leg holes, opposite side regions, an elastic waist portion disposed along said waist hole, and a leg gather disposed along each of said leg holes;

said main body comprising separately produced front and rear sections, said front section comprising a first backsheet formed from material supplied from a first backsheet web, a first topsheet formed from material supplied from a first topsheet web, and a first absorbent body interposed between said first topsheet and said first backsheet, and said rear section comprising a second backsheet formed from material supplied from a second backsheet web, a second topsheet formed from material supplied from a second topsheet web and a second absorbent body interposed between said second topsheet and said second backsheet, said separately produced front and rear sections being joined so that their respective topsheets face each other and are bonded to each other in the crotch region and opposite side regions of the article.

2. The absorbent article of claim 1, wherein said front and rear sections respectively have portions extending laterally outwardly from the absorbent body and secured in facing relation to each other in said crotch and opposite side regions of the article.

3. The absorbent article of claim 1, wherein said leg gather comprises a member disposed on a top surface of each of said front section and said rear section, said member having a proximal end disposed adjacent to said top surface and a distal end spaced away from said top surface, said member being secured onto itself at a location adjacent to the crotch region where said front section and rear section are bonded to each other.

4. The absorbent article of claim 1, wherein said backsheet of the rear section is comprised of an elastically stretchable and contractible material.

5. The absorbent article of claim 4, wherein said elastically stretchable and contractible material comprises an elastic composite, said elastic composite is formed from a liquid impermeable, elastic material and a non-woven fabric, said liquid impermeable, elastic material comprising said second backsheet and said non-woven fabric comprising said second topsheet.

6. The absorbent article of claim 2, wherein said portions are secured to each other by hotmelt adhesives.

7. The absorbent article of claim 1, wherein said front section and rear section have tabs at their respective ends, adjacent the crotch region and said tabs are secure to each other by hotmelt adhesives, said article further having a reinforcing member secured in the crotch region and extending along a boundary line between said front section and said rear section.

8. The absorbent article of claim 1, wherein a projecting separator petal is disposed along a boundary line between said front section and said rear section in said crotch region for separating solid exudates from liquid exudates.

9. The absorbent article of claim 1, wherein said front section and said rear section are joined to each other by elastic side panels attached to respective opposite sides of the front and rear sections.

10. The absorbent article of claim 1, wherein said rear section further comprises a barrier cuff spaced away from the topsheet to define a space therebetween, said barrier cuff having an opening for receiving exudates into said space.

11. The absorbent article of claim 1, wherein an absorbent pad is disposed between said front section and said rear section, said absorbent pad is joined at one end to a securement region of said front and rear sections so that the absorbent pad is movable between a first position on the topsheet of the front section and a second position on the topsheet of the rear section.

12. An absorbent article comprising:

a main body having a waist hole and a pair of leg holes, a crotch region between the leg holes, opposite side regions, an elastic waist portion disposed along said waist hole and leg gathers disposed along each of said leg holes;

said main body comprising separately produced front and rear sections, each of said front and rear sections comprising a backsheet formed from materials supplied from respective first and second backsheet webs, a topsheet formed from materials supplied from respective first and second topsheet webs, an absorbent body interposed between said topsheet and said backsheet, said separately produce front and rear sections being joined so that their respective topsheet face each other and are bonded to each other in the crotch region and opposite side regions of the article, said front section having at least one constituent element whose property is different from that of the corresponding element of the rear section, and said leg gather of each of said front and rear sections being at an end secured onto itself in the crotch region of the main body to define a cross-over flap of substantially triangular shape extending inwardly of said leg gather so that said leg gather stands up from the topsheet.

* * * * *